United States Patent
Fawdington et al.

(10) Patent No.: US 10,138,042 B2
(45) Date of Patent: Nov. 27, 2018

(54) CONTACT LENS DISPENSING CONTAINER

(71) Applicant: Optic 18 Limited, Loughborough (GB)

(72) Inventors: Keith Fawdington, Loughborough (GB); Jayesh Ghadiali, Nottingham (GB)

(73) Assignee: Optic 18 Limited, Loughborough (GB)

( * ) Notice: Subject to any disclaimer, the term of this patent is extended or adjusted under 35 U.S.C. 154(b) by 468 days.

(21) Appl. No.: 14/710,239

(22) Filed: May 12, 2015

(65) Prior Publication Data

US 2016/0198825 A1    Jul. 14, 2016

(30) Foreign Application Priority Data

Jan. 14, 2015   (GB) .................................. 1500560.6

(51) Int. Cl.
*A61F 9/00*     (2006.01)
*B65D 75/32*    (2006.01)
*A45C 11/00*    (2006.01)

(52) U.S. Cl.
CPC .......... *B65D 75/326* (2013.01); *A45C 11/005* (2013.01); *A61F 9/0061* (2013.01); *B65D 2585/545* (2013.01)

(58) Field of Classification Search
CPC ............ B65D 2585/545; B65D 75/326; A61F 9/0061; A45C 11/005; A45C 2011/006; A45C 11/046
USPC ........................................................ 206/5.1
See application file for complete search history.

(56) References Cited

U.S. PATENT DOCUMENTS

| | | | | |
|---|---|---|---|---|
| 5,409,104 A | * | 4/1995 | Lovell | B65D 75/32 206/467 |
| 5,609,246 A | * | 3/1997 | Borghorst | A61F 2/1691 134/901 |
| 5,695,049 A | | 12/1997 | Bauman | |
| 2008/0047848 A1 | * | 2/2008 | Tokarski | A45C 11/005 206/5.1 |
| 2014/0027465 A1 | * | 1/2014 | Howell | B65D 75/326 221/154 |

FOREIGN PATENT DOCUMENTS

WO       2006/105179 A1    10/2006

* cited by examiner

*Primary Examiner* — Steven A. Reynolds
(74) *Attorney, Agent, or Firm* — Hoffmann & Baron, LLP

(57) ABSTRACT

A contact lens dispensing container includes an upwardly opening receptacle, peelable cover sheet, and applicator. The receptacle is to receive a contact lens and storage solution, and the container having a peripheral flange providing a planar engagement surface surrounding the receptacle. The cover sheet is securable to the engagement surface to seal the container and peelable from the engagement surface to allow lens removal. The applicator includes a handle having first end and second end. The handle is pivotably mounted on the flange and having a carrier at the first end and a hand grip at the second end. The applicator is moveable between stowed position and deployed position, wherein in stowed position the carrier is received in the receptacle with the handle not extending above the engagement surface, and in deployed position the applicator is rotated from the stowed position so that the carrier is above the engagement surface.

14 Claims, 4 Drawing Sheets

CONTACT LENS DISPENSING CONTAINER

CROSS-REFERENCE TO RELATED APPLICATION

This application claims priority to Great Britain Patent Application No. 1500560.6, filed on Jan. 14, 2015, the contents of which are incorporated herein by reference in their entirety.

BACKGROUND

Field

This invention relates to a container in which a contact lens is stored after manufacture from which the lens may be dispensed for use by a wearer.

Brief Discussion of Related Art

Conventional contact lens dispensing containers comprise a receptacle covered with a peelable foil sheet. When the wearer receives a container with a new lens, the foil sheet is removed and the storage solution and lens are tipped onto a user's palm after which a finger is inserted into the lens to pick it up. Alternatively a finger may be placed directly into the solution to remove the lens. The lens is then inserted onto the eye by the wearer by placing the finger onto the eye. This procedure can be disadvantageous if the user's finger and hand are not clean and sterile. Also, the lens may be difficult to locate visually and to manipulate as it is composed of transparent material. Further, there is a risk that the lens can be dropped, resulting in contamination or loss of the lens.

SUMMARY

According to the present invention a contact lens dispensing container comprises: an upwardly opening receptacle configured to receive a single contact lens and storage solution, the container having a peripheral flange providing a planar engagement surface surrounding the receptacle;

a peelable cover sheet securable to the engagement surface to seal the container and peelable from the engagement surface to allow removal of the content lens in use;

an applicator comprising a handle having first and second ends, the handle being pivotably mounted on the flange, having a carrier adapted to carry a contact lens in use, the carrier being located at the first end of the handle and a hand grip located at the second end of the handle;

the applicator being moveable between stowed and deployed positions, wherein in the stowed position the carrier is received in the receptacle with the handle not extending above the engagement surface, and in the deployed position the applicator is rotated from the stowed position so that the carrier is located above the engagement surface to facilitate direct application of the contact lens carried by the carrier onto a wearer's eye.

The dispensing container of the present invention has the advantage that the new lens may be dispensed from the container directly to a user's eye without the need for manual contact. This avoids a risk of contamination from a wearer's finger. After use the contact lens may be disposed of or may be removed and stored in a conventional container into which cleaning or disinfecting solution may be added. The present container is not intended for storage of a contact lens after use.

The receptacle and handle are preferably a unitary construction, for example formed from moulded polyethylene, polypropylene or other polymer which is sufficiently rigid and resilient to permit flexing of the hinge in use without offering excessive resistance to rotation or on the other hand a liability to fracture. The hinge may comprise a region of reduced thickness allowing the applicator to be pivotally moved relative to the receptacle. Alternatively, a pivoted linkage may be provided between the receptacle by a relatively flexible region and handle.

The handle may be laminar and co-planar with the hand grip. The handle may extend outwardly from the container and configured to facilitate gripping between a wearer's finger and thumb during use.

The carrier of the applicator may include an aperture to permit drainage of storage solution. The carrier may include a partially spherical holder for a contact lens and may have the configuration of a partially spherical or concave configuration basket or frame. Alternatively, a partially spherical or concave configuration may be used. Such an arrangement may facilitate drainage of the storage solution as the hinge is raised from the receptacle.

In an alternative embodiment, the handle may be detachable from the flange. The handle may be attached by a frangible coupling or linkage. A web of reduced thickness or having perforations may be employed. Alternatively, the handle may be attached to the flange by a snap-fit coupling arranged so that the handle may be separated from the flange as it is rotated from the stowed position towards a deployed position. For example, pins or other perforations extending from the handle may be received within sockets in the flange, one or both of the pins and sockets being resiliently deformable or frangible. Alternatively, pins or projections may extend from the flange into sockets in the handle. In a further alternative embodiment, the handle and flange may be retained in the stowed position by the peelable cover sheet, so that the handle may be freed for deployment when the cover sheet is removed or torn by rotation of the handle.

In an alternative embodiment the handle may be formed from a separate component, pivotally secured to the flange for example by a ball and socket or snap-fit hinge arrangement wherein projections from the handle or flange extend into respective sockets in the flange or handle respectively.

Alternatively, a hinge pin arrangement may be used.

In a preferred embodiment a second hand grip extends from the flange at a location remote from the hinge. This enables the wearer to hold the receptacle in one hand while dispensing the contact lens with the other hand.

The handle is preferably formed from a laminar member. The member may be received in a rebate in the flange in the stowed position. The handle may be received beneath the flange in a fully opened position of the applicator.

The receptacle may be formed of flexible material which may be deformed by upward pressure from a user's finger to urge the handle from the receptacle during dispensing. The receptacle may be formed from a thin and easily flexible sheet or film of material to facilitate dispensing in this way.

The receptacle may be any convenient shape, for example partially spherical to cooperate with the lower surface of the carrier and to minimise the volume of storage solution required.

In an alternative embodiment, two receptacles may be mounted side by side or end to end so that two lenses may be dispensed in a single pack.

In use the peelable cover sheet serves to retain the carrier of the applicator within the chamber of the receptacle. The receptacle, applicator and cover sheet form a sealed container within which the contact lens and storage solution are retained in a sterile environment during storage and transportation before use.

BRIEF DESCRIPTION OF THE DRAWINGS

The invention is further described by means of example but not in any limitative sense with reference to the accompanying drawings of which.

DETAILED DESCRIPTION

The contact lens dispensing container shown in FIGS. 1 to 6 comprises a rigid polymeric receptacle (1) forming a part spherical well to receive a contact lens (2) and a quantity of storage solution.

Figure 6:
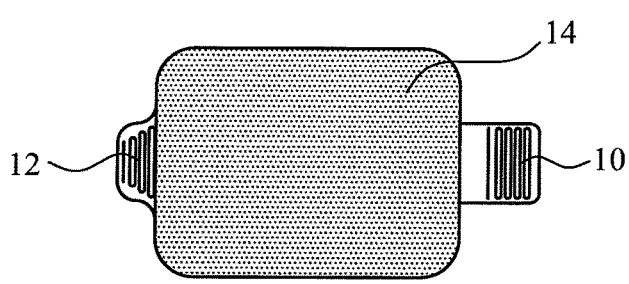
Figure 7:
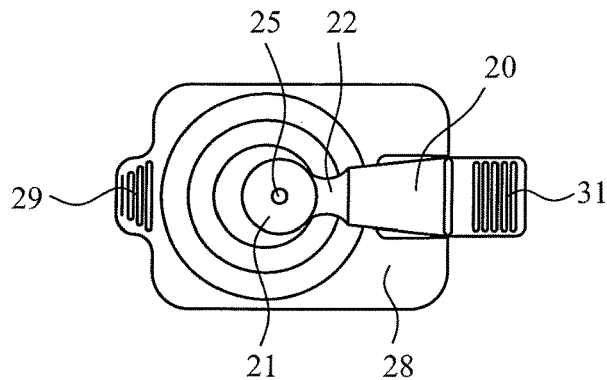
FIGS. 7 to 14 illustrate an alternative embodiment of the invention.
Figure 8:
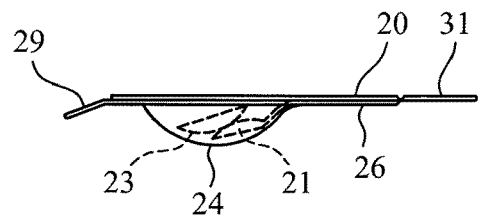
Figure 9:
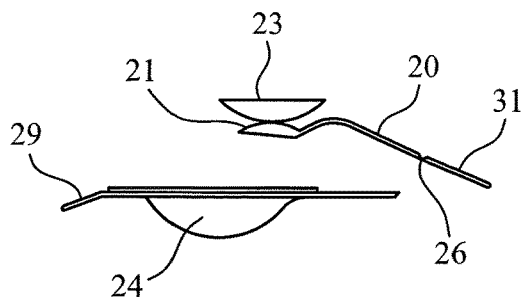
Figure 10:
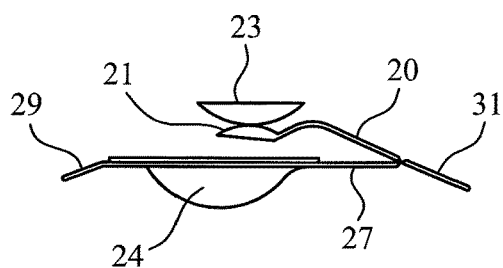
Figure 11:
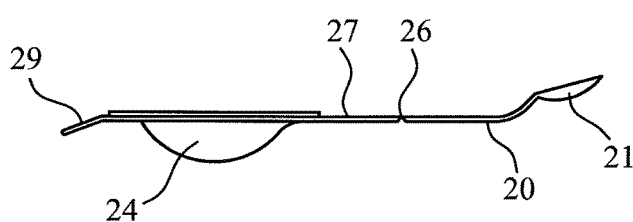
Figure 12:
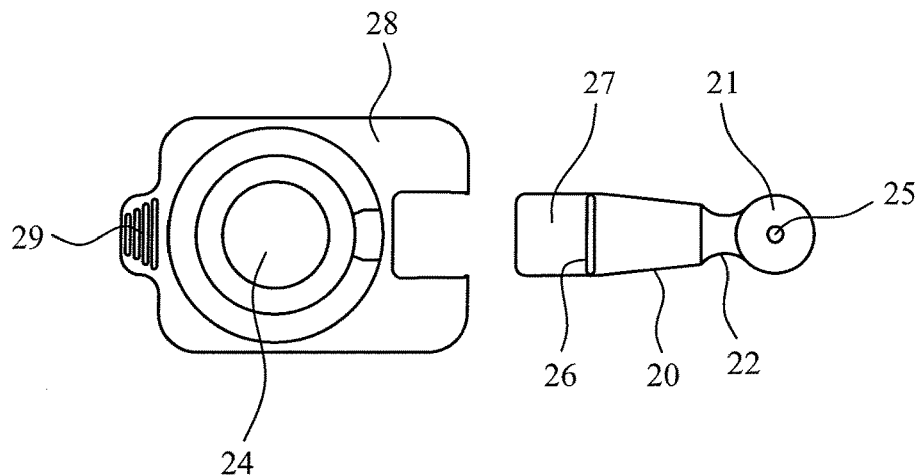
Figure 13:
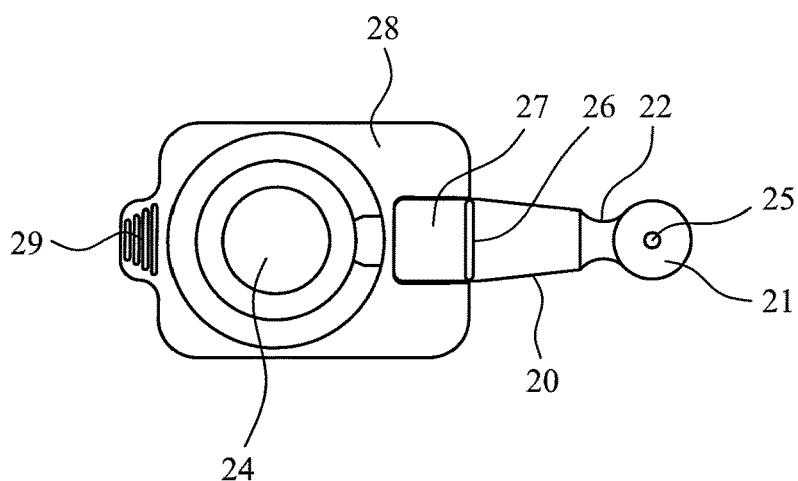
Figure 14:
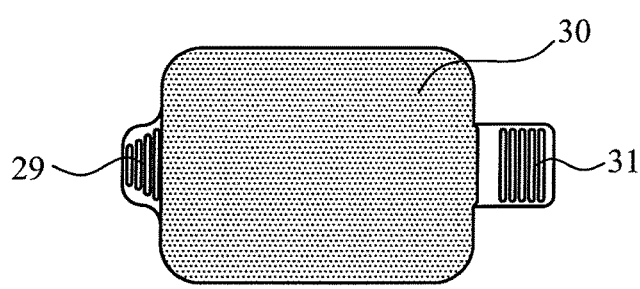

A rectangular flange (3) extends around the upper periphery of receptacle (1) to form a complete circumferential engagement surface onto which a peelable sheet (14) may be secured as shown in FIG. 6 in order to form a sealed container for the contact lens and storage solution.

An applicator comprises a handle (5) having a first end (6) and a second end (7). The second end (7) is attached by an integral three-way hinge (9) to the flange (3) and to a hand grip (10). The handle (5) and hand grip (10) form a continuous member pivotable about the hinge (9) relative to the flange (3). The first end of the handle comprises a carrier (8). The carrier may comprise a spoon-like concave receptacle having a drainage hole (11) to permit drainage of storage solution as the receptacle is raised.

Alternatively, the carrier may have a lattice or basket-like configuration or may comprise a number of outwardly extending arms to support a lens without preventing fluid flow as the lens is raised from the storage solution.

A hand grip (12) extends from the flange opposite to the applicator and hand grip (10).

When assembled for storage of a contact lens, the handle is located above or co-planar with the flange (3) so that the carrier (8) is disposed completely within the receptacle. The contact lens is then placed onto the carrier (8) and the storage solution added. Finally, the foil or polymeric cover sheet (14) is applied to form a sealed enclosure for transportation and storage of the lens until it is dispensed. The top surface of the peelable sheet may be printed with information about the prescription and other characteristics of the lens as shown in FIG. 6.

Figure 1:
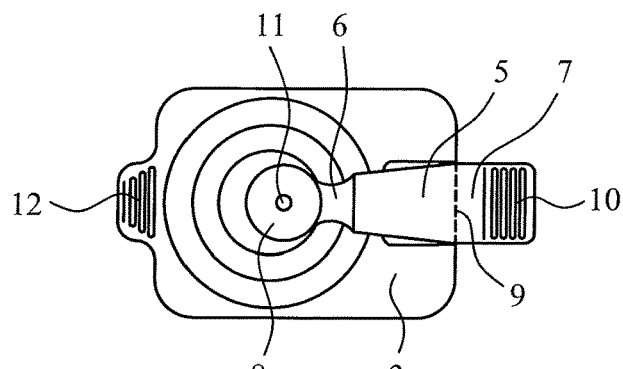
FIGS. 1 to 6 show an applicator in accordance with this invention.
Figure 2:
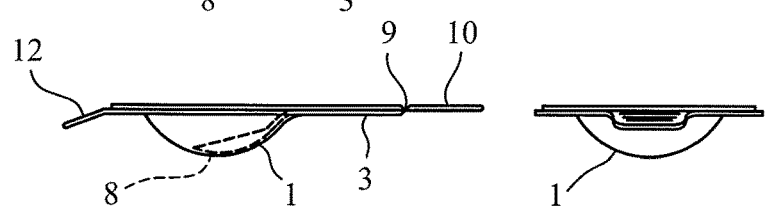
Figure 3:
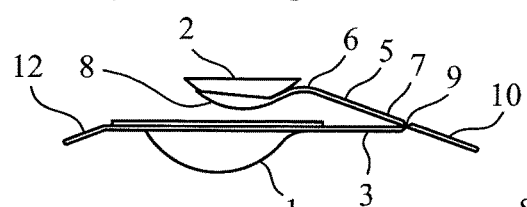

When the sheet (14) is removed by peeling from the flange (3), the container appears as shown in FIG. 1 or 2. A user can hold the left and right grips (12, 10) with the fingers of each hand. Rotation of the hand grip (10) downwardly about the hinge (9) causes the handle (5) to be raised, lifting the carrier (8) and lens (2) from the solution, as shown in FIG. 3. In this position the container may be raised towards a user's eye so that the lens may be placed directly upon the user's eyeball without any need for touching the lens or tipping it into the palm of a user's hand.

Figure 4:
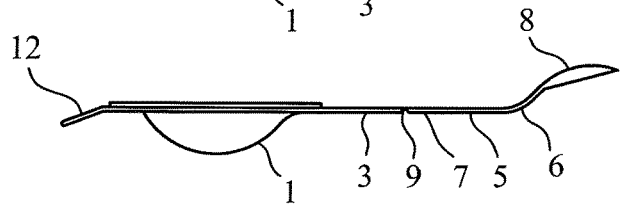
Figure 5:
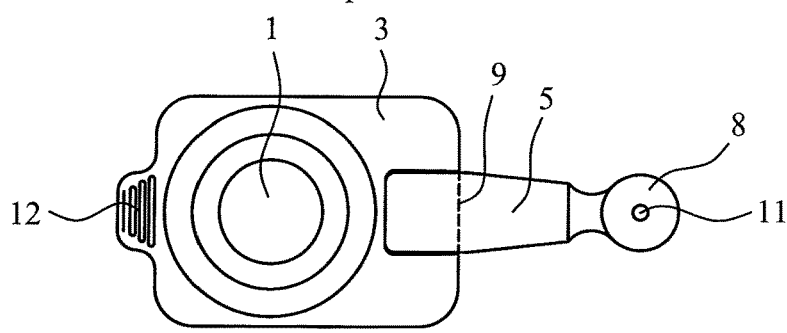

FIGS. 4 and 5 show a fully opened position in which the arm and carrier are extended away from the receptacle. In this arrangement, the storage fluid may be poured from the receptacle.

The receptacle and applicator may be formed from a unitary moulding so that the hinge (9) forms a flexible region of reduced thickness. Alternatively, the handle and receptacle may be formed from separate components hingeably mounted by a ball and socket arrangement or by a hinge in which axle stubs extend from the handle into bearing sockets of the flange. The handle may be detachable from the receptacle as described with reference to the following figures.

FIGS. 7 to 14 illustrate an alternative embodiment of the invention, wherein the handle (20) has a neck (22) supporting a carrier with a convex upwardly facing support structure (21) upon which a contact lens (23) may rest as the handle and contact lens are moved from the stowed to the deployed position. The lens (23) contacts the central raised portion of the carrier (8) permitting storage solution to drain from the lens back into the receptacle (24), reducing adhesion of the lens to the carrier. A circular central aperture (25) is provided to promote engagement of the lens upon the support structure as the carrier is raised from the storage solution in the receptacle (24).

Handle (20) is connected by hinge (26) to a planar member (27). Planar member (27) is generally rectangular in plan view and is detachably engaged within a correspondingly shaped aperture in flange (28). This arrangement allows the handle (20) copper support structure (21) and planar member (27) to be detached from the flange (28) and receptacle (24) to facilitate application of the contact lens to a user's eye.

In use of the container a user may hold the container using the hand grip (29) while the foil cover sheet (30) (shown in FIG. 14) is peeled from the flange (28). Then the hand grip (31) may be grasped to rotate the handle (20) and detach the handle and planar member (27) from the flange (28) of the receptacle. The lens may then be conveniently located onto a user's eyeball.

The dimensions of the components of the container are preferably selected so that the lens conveniently rests upon the carrier during storage without a need for manual adjustment during movement to the deployed position.

In a preferred embodiment the receptacle may have a diameter at the upper surface of 19.5 mm to 20 mm and a length around the curved lower surface of 22 mm with a depth of 4.5 mm to 5 mm. The carrier (21) may have a diameter of 10 mm so that a lens with a typical diameter of 14 mm may rest conveniently upon the carrier (21) in the stowed position shown in FIG. 9. Typically the contact lens may have a diameter of 14 mm and a radius of 8.3 mm to 8.7 mm, typically 8.6 mm. Preferably the receptacle may have a diameter of 1.2 mm to 1.5 mm, typically about 1.3 mm of the diameter of the lens.

Figure 15:
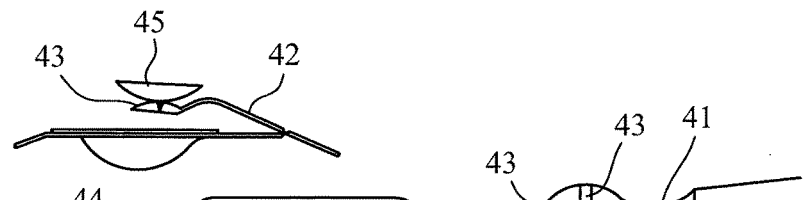
FIGS. 15 to 18 illustrate further embodiments of the invention.
Figure 15:
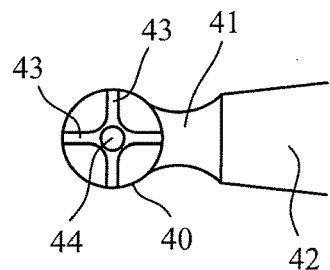

FIGS. 15 to 18 illustrate alternative embodiments of the invention. In FIG. 15 the carrier (40) mounted on a neck (41) on handle (42), has an upwardly curved convex configuration with four perpendicular drainage channels (43) connected to a central aperture (44) to permit convenient drainage of storage solution from the undersurface of the lens (45).

Figure 16:
Figure 16:
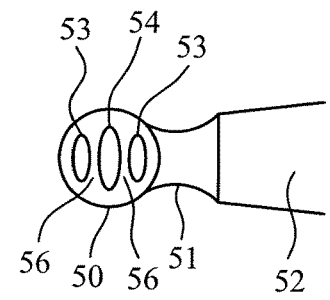

FIG. 16 illustrates an alternative embodiment in which the support member (50) and neck (51) are mounted on handle (52) has three upwardly extending projections (53, 54) arranged to engage and support the lower surface of lens (55), providing drainage channels (56) between the projections. The central projection (54) is larger than the two outer projections (53) to support a lens (55) preventing it from tipping sideways during insertion into a user's eye.

Figure 17:
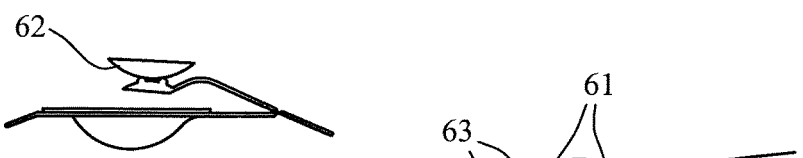
Figure 17:
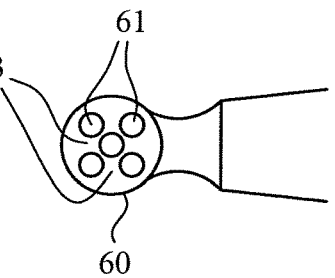

FIG. 17 illustrates a further embodiment in which the body (60) has four upwardly extending projections (61) having upwardly facing contact surfaces arranged to engage the lower surface of a lens (62) providing drainage channels (63) between the projections to facilitate drainage of storage fluid.

Figure 18:
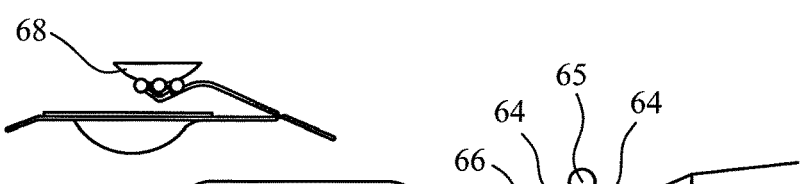
Figure 18:
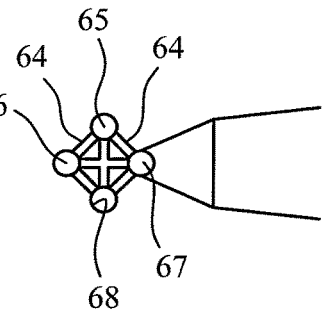

FIG. 18 shows a further embodiment in which the body is formed from a support frame comprising arms (64) extending between spherical or rounded projections (65, 66, 67), each projection having an upper facing support surface to engage the surface of a lens (68). The arms (64) have apertures between adjacent arms (64) allow for convenient drainage of storage soluble.

The invention claimed is:

1. A contact lens dispensing container comprising:
   an upwardly opening receptacle configured to receive a single contact lens and storage solution;
   a peripheral flange providing a planar engagement surface surrounding the receptacle;
   a peelable cover sheet securable to the engagement surface to seal the receptacle, the peelable cover peelable from the engagement surface to allow removal of the contact lens from the receptacle;
   an applicator comprising a handle, the handle having a first end and a second end, the handle being pivotably mounted on the flange and having a carrier located at the first end of the handle and a hand grip located at the second end of the handle, the handle and the hand grip forming a continuous member pivotable at the second end of the handle relative to the flange; and
   the applicator being moveable between a stowed position and a deployed position, wherein in the stowed position the carrier is received in the receptacle with the handle not extending above the engagement surface, and in the deployed position the hand grip is rotated in relation to the flange causing the handle to be raised so that the carrier is located above the engagement surface to facilitate direct application of the contact lens from the carrier onto a wearer's eye without need for manual contact.

2. The contact lens dispensing container as claimed in claim 1, wherein the receptacle and handle are a unitary construction.

3. The contact lens dispensing container as claimed in claim 1, wherein the handle is detachable from the receptacle.

4. The contact lens dispensing container as claimed in claim 1, wherein a hinge comprises a region of reduced thickness.

5. The contact lens dispensing container as claimed in claim 1, wherein the handle is laminar.

6. The contact lens dispensing container as claimed in claim 1, wherein the handle and hand grip are co-planar in the stowed position.

7. The contact lens dispensing container as claimed in claim 1, wherein the applicator includes an aperture to permit drainage of storage solution.

8. The contact lens dispensing container as claimed in claim 1, wherein a second hand grip extends from the flange to a location remote from a hinge.

9. The contact lens dispensing container as claimed in claim 1, wherein the handle is laminar and received in a rebate in the flange in the stowed position.

10. The contact lens dispensing container as claimed in claim 1, wherein a pivot point of a hinge is on an upper surface of the flange.

11. The contact lens dispensing container as claimed in claim 10, wherein the pivot point of the handle comprises an edge of the flange.

12. The contact lens dispensing container as claimed in claim 1, wherein the applicator is enabled to be urged to a position at an angle of 10° to 70° relative to the flange on removal of the peelable cover sheet.

13. The contact lens dispensing container as claimed in claim 12, wherein the angle is 30° to 50°.

14. A contact lens pack comprising:
    a first contact lens dispensing container comprising:
        a first upwardly opening receptacle configured to receive a first single contact lens and first storage solution;
        a first peripheral flange providing a first planar engagement surface surrounding the first receptacle;
        a first peelable cover sheet securable to the first engagement surface to seal the first receptacle, the first peelable cover peelable from the first engagement surface to allow removal of the first contact lens from the first receptacle;
        a first applicator comprising a first handle, the first handle having a first end and a second end, the first handle being pivotably mounted on the first flange and having a first carrier located at the first end of the first handle and a first hand grip located at the second end of the first handle, the first handle and the first hand grip forming a continuous member pivotable at the second end of the first handle relative to the first flange; and
        the first applicator being moveable between a first stowed position and a first deployed position, wherein in the first stowed position the first carrier is received in the first receptacle with the first handle not extending above the first engagement surface, and in the first deployed position the first hand grip is rotated in relation to the first flange causing the first handle to be raised so that the first carrier is located above the first engagement surface to facilitate direct application of the first contact lens from the first carrier onto a wearer's eye without need for manual contact; and
    a second contact lens dispensing container conjoined with the first contact lens dispensing container, the second contact lens dispensing container comprising:
        a second upwardly opening receptacle configured to receive a second single contact lens and second storage solution;
        a second peripheral flange providing a second planar engagement surface surrounding the second receptacle;
        a second peelable cover sheet securable to the second engagement surface to seal the second receptacle, the second peelable cover peelable from the second engagement surface to allow removal of the second contact lens from the second receptacle;
        a second applicator comprising a second handle, the second handle having a first end and a second end, the second handle being pivotably mounted on the second flange and having a second carrier located at the first end of the second handle and a second hand grip located at the second end of the second handle;
        the second applicator being moveable between a second stowed position and a second deployed position, wherein in the second stowed position the second carrier is received in the second receptacle with the second handle not extending above the second engagement surface, and in the second deployed position the second applicator is rotated in relation to the second flange from the second stowed position so that the second carrier is located above the second engagement surface to facilitate direct application of the second contact lens from the second carrier onto a wearer's eye without need for manual contact.

* * * * *